United States Patent [19]

Terasawa et al.

[11] Patent Number: 5,153,123
[45] Date of Patent: * Oct. 6, 1992

[54] METHOD FOR PRODUCING L-THREONINE, AND PLASMID AND MICROORGANISM EMPLOYED IN THE SAME

[75] Inventors: Masato Terasawa; Terukazu Nara; Makiko Fukushima; Yukie Satoo; Mitsunobu Shimazu; Hideaki Yukawa; Yasurou Kurusu; Keiko Kohama, all of Ibaraki, Japan

[73] Assignee: Mitsubishi Petrochemical Co., Ltd., Tokyo, Japan

[ * ] Notice: The portion of the term of this patent subsequent to May 28, 2008 has been disclaimed.

[21] Appl. No.: 257,524

[22] Filed: Oct. 14, 1988

[30] Foreign Application Priority Data

Oct. 15, 1987 [JP] Japan .................................. 62-260556
Apr. 7, 1988 [JP] Japan .................................... 63-83993

[51] Int. Cl.$^5$ .................................................. C12P 13/08
[52] U.S. Cl. ...................................... 435/115; 435/840
[58] Field of Search ................................ 435/115, 840

[56] References Cited

U.S. PATENT DOCUMENTS

| | | | |
|---|---|---|---|
| 3,494,830 | 2/1970 | Nakayama et al. | 435/115 |
| 3,582,471 | 6/1971 | Shiio et al. | 435/840 |
| 5,019,503 | 5/1991 | Terasawa et al. | 435/115 |

FOREIGN PATENT DOCUMENTS

| | | |
|---|---|---|
| 82485 | 6/1983 | European Pat. Off. . |
| 88166 | 9/1983 | European Pat. Off. . |
| 137348 | 4/1985 | European Pat. Off. . |
| 57-155996 | 9/1982 | Japan . |

OTHER PUBLICATIONS

Gottschalk, *Bacterial Metabolism*, p. 41, 1979.

*Primary Examiner*—Douglas W. Robinson
*Assistant Examiner*—Jean C. Witz
*Attorney, Agent, or Firm*—Oblon, Spivak, McClelland, Maier & Neustadt

[57] ABSTRACT

A method for producing L-threonine, which comprises subjecting at least L- or DL-aspartic acid or a salt thereof to enzymatic reaction according to the reaction system not accompanied with growth of microorganism cells in an aqueous solution in the presence of a microorganism and collecting L-threonine formed, wherein the microorganism is a biotin-requiring microorganism for the growth belonging to coryneform bacterium; a plasmid comprising a DNA fragment containing at least a gene encoding biosynthesis of threonine which can be expressed within a biotin-requiring microorganism cell for the growth belonging to coryneform bacterium and a DNA fragment containing a gene encoding autonomous replication within coryneform bacterium cell; and a biotin-requiring microorganism for the growth belonging to coryneform bacterium which has been transformed with the plasmid described above, both of which are employed in the present method.

According to the present invention, L-threonine can be produced with good yield, and further since production management becomes extremely easy without requiring cumbersome operation such as sterilization of the medium, etc. as in the fermentation method, L-threonine can be produced inexpensively in industry.

2 Claims, No Drawings

METHOD FOR PRODUCING L-THREONINE, AND PLASMID AND MICROORGANISM EMPLOYED IN THE SAME

BACKGROUND OF THE INVENTION

This invention relates to a method for producing L-threonine, and to a plasmid and a microorganism employed in the method.

L-threonine is an amino acid which plays an important role in nutrition for human beings and animals as an essential amino acid, and its demand for pharmaceuticals, foods, fodder potentiating agent is abruptly increasing in recent years.

With respect to an industrial production method of L-threonine, because of existence of stereoisomers similarly as other amino acids, production of only the L-isomer is difficult by chemical synthesis, and it is primarily produced by the fermentation method. As the method for producing it by the fermentation method, there may be included a method by use of an amino acid-requiring strain (Japanese Patent Publications Nos. 3319/1971, 34193/1971, 34194/1971, etc.). Methods for producing it by the precursor fermentation method include, a method by use of homoserine as the precursor (Japanese Patent Publications Nos. 2896/1961, 6590/1963, 8715/1968, etc.).

However, such fermentation methods cannot be said to be industrially advantageous methods for such reasons that cumbersome operations such as sterilization of medium, etc. are required, that there is the problem of by-products and also that the production management is extremely difficult.

On the other hand, among enzymatic production methods which are less expensive in fixed cost and easier in production management than the fermentation method, there have been proposed a method by the use of glycine and acetaldehyde as precursors (Japanese Unexamined Patent Publications Nos. 121491/1981, 116681/1983, etc.), but this method involves formation of a by-product, allotype threonine, and therefore are not practical methods.

Otherwise, for the production method according to the enzyme method, it has been reported to form L-threonine with a reaction mixture in which DL-homoserine is permitted to exist by use of various microorganism cells (Amino Acids, vol. 1, p. 71-74 (1959)).

However, according to these known methods, the amount of L-threonine formed is not yet satisfactory.

The present inventors have intensively studied in order to produce L-threonine industrially at low cost with good yield, and consequently accomplished the present invention.

SUMMARY OF THE INVENTION

The present invention provides a method for producing L-threonine, which comprises subjecting at least L- or DL-aspartic acid or a salt thereof to enzymatic reaction according to the reaction system not accompanied with growth of microorganism cells in an aqueous solution in the presence of a microorganism and collecting or recovering L-threonine formed, wherein said microorganism requires biotin for growth and belongs to *Coryneform bacteria*.

In one of the preferred embodiments of the present invention, the microorganism is one transformed with a plasmid comprising a DNA fragment containing the gene encoding the enzymes participating in biosynthesis of threonine (threonine operon) which can be expressed in a biotin-requiring microorganism for the growth belonging to coryneform bacteria and a DNA fragment containing a gene encoding autonomous replication in coryneform bacteria cell.

Namely, in one of preferred embodiments of the present invention, the method comprises subjecting at least L- or DL-aspartic acid or a salt thereof to enzymatic reaction according to the reaction system not accompanied with growth of microorganism cells in an aqueous solution in the presence of a microorganism and collecting L-threonine formed, wherein said microorganism requires biotin for growth belonging to coryneform bacteria which has been transformed with the above described plasmid.

The present invention therefore also provides the above described plasmid and the above described microorganism employed in the present method.

DESCRIPTION OF THE PREFERRED EMBODIMENTS

According to the present invention, L-threonine can be produced with good yield, and further since production management becomes extremely easy without requiring cumbersome operations such as sterilization of the medium, etc. as in the fermentation method, L-threonine can be produced inexpensively in industry.

Further, when the present microorganism transformed with the present plasmid is employed in the present method, particularly excellent effects can be obtained.

Moreover, when a reaction solution containing ethanol and/or glucose is used as an aqueous solution for the enzymatic reaction, effects of the present invention can be accelerated.

The biotin-requiring microorganism for the growth belonging to coryneform bacteria to be used in the present invention may include *Brevibacterium flavum* or a strain derived therefrom, and preferably *Brevibacterium flavum* MJ-233 as exemplified by a microorganism having an ethanol-utilizing property, such as *Brevibacterium flavum* MJ-233 (FERM BP-1497), *Brevibacterium flavum* MJ-233-AB-41 (FERM BP-1498), *Brevibacterium flavum* MJ-233-ABT-11 (FERM BP-1500) and *Brevibacterium flavum* MJ-233-ABD-21 (FERM BP-1499). In addition to the above described ones, *Brevibacterium ammoniagenes* ATCC 6871, ATCC 13745, ATCC 13746, *Brevibacterium divaricatum* ATCC 14020 can be also exemplified.

Among the microorganisms described above, ones having an ethanol-utilizing property are preferable and *Brevibacterium flavum*, FERM BP-1487, *Brevibacterium flavum* MJ-233-AB-41 FERM BP-1498, *Brevibacterium flavum* FERM BP-1500 and *Brevibacterium flavum* FERM BP-1499 are particularly preferable.

These microorganisms have been deposited at Fermentation Research Institute, Agency of Industrial Science and Technology, Japan, under the Budapest Treaty, and are freely available to the public.

The *Brevibacterium flavum* MJ-233-AB-41 (FERM BP-1498) is a microorganism having an ethanol-utilizing property to which DL-α-aminobutyric acid resistance is positively imparted by use of *Brevibacterium flavum* MJ-233 (FERM BP-1497) as a parent strain (See Japanese Patent Publication No. 28398/1984, columns 3 to 4). The *Brevibacterium flavum* MJ-233-ABT-11 (FERM BP-1500) is L-α-aminobutyric acid trans aminase high activity mutant by use of *Brevibacterium flavum* MJ-233 (FERM BP-1497) as a parent strain (see Japanese Unexamined Patent Publication No. 51998/1987. Further, the *Brevibacterium flavum* MJ-233-ABD-21 (FERM BP-1499) is D-α-aminobutyric acid deaminase high activity mutant by use of *Brevibacterium flavum* MJ-233 (FERM BP-1497) as a parent strain (see Japanese Unexamined Patent Publication No. 177993/1986).

Generally speaking, microorganism strains begin to undergo lysis phenomenon when thier cell division can be inhibited.

In the production method of the present invention, for producing L-threonine with good yield, it is preferable that the cell reaction can be continued for a long term. In the above *Brevibacterium flavum* MJ-233 or microorganism strains derived therefrom, even under the conditions where cell division is inhibited, no lysis phenomenon is recognized, and therefore it is particularly preferably used in the production method of the present invention.

In the production method of the present invention, the above microorganism strains may also be immobilized. Such immobilization can be practiced by immobilizing the above microorganism strains according to the known immobilization methods as suitably selected from, for example, the inclusion method with acrylamide, alginate, carageehnan, etc., the ion bonding method with DEAE-Sephadex, DEAE-cellulose, etc.

The production method of the present invention may be performed in an aqueous solution, and as the aqueous solution, water or a buffer solution such as phosphate or Tris hydrochloride, etc. may usually be used, and preferably ethanol, glucose either alone or in combination may be contained therein.

The aqueous solution may further contain nitrogen sources, inorganic salts, etc. As such nitrogen sources, there may be included, for example, ammonia, ammonium sulfate, ammonium chloride, ammonium nitrate, urea, etc. As the inorganic salt, there may be included, for example, potassium monohydrogen phosphate, potassium dihydrogen phosphate, magnesium sulfate, iron sulfate, manganese sulfate, etc. When a nitrogen source or an inorganic salt is to be contained, for inhibiting growth of the above microorganism strains, it is necessary to remove biotin which is the essential factor for growth from the aqueous solution.

The concentrations of ethanol and glucose to be added in the aqueous solution may be generally 1 to 20 vol. % in case of ethanol, generally 0.5 to 20 vol. % in case of glucose, and when both are used in combination, each may be used at the respective concentrations within the above ranges.

The concentration during the reaction of L- or DL-aspartic acid or a salt thereof may be generally 0.1 to 20% (wt./vol.). As the salts of aspartic acid to be used here, there may be included, for example, sodium aspartate, calcium aspartate, potassium aspartate, etc.

The amount of the biotin-requiring microorganism used is not particularly limited, but generally 1 to 50% (wt./vol.).

The enzymatic reaction according to the reaction system not accompanied with growth of microorganism cells is carried out generally at about 20° C. to about 50° C., preferably about 30° to about 40° C., generally for about 10 to about 72 hours.

Separation and purification of the L-threonine formed in the reaction mixture according to the reaction method as described above can be performed easily by way of ion-exchange resin treatment method or the precipitation method, etc.

The above biotin requiring microorganism strain capable of forming L-threonine from aspartic acid can be cultured as described below.

As the carbon source, for example, glucose, ethanol, methanol, waste molasses, etc., as the nitrogen source, for example, ammonia, ammonium sulfate, ammonium chloride, ammonium nitrate, urea, etc. can be used each individually or as a mixture of them. As the inorganic salt, for example, potassium monohydrogen phosphate, potassium dihydrogen phosphate, magnesium sulfate, iron sulfate, manganese sulfate, etc.

Otherwise, nutrient ingredients such as peptone, meat extract, yeast extract, corn steep liquor, casamino acid and various vitamins such as biotin, etc. may be also added into the medium.

Culturing is conducted under aerobic conditions such as aerated stirring, shaking, etc., and the culture temperature may be generally 20° to 40° C., preferably 25° to 35° C. The pH in the course of culturing may be generally 5 to 10, preferably around 7 to 8, and the pH during culturing can be adjusted by addition of an acid or an alkali.

When ethanol is used as the carbon source, the concentration at initiation of cultivation may be preferably 1 to 5 vol. %, more preferably 2 to 3 vol. %. The cultural period may be generally 2 to 9 days, preferably 4 to 7 days.

The microorganism cells are collected from the cultured product thus obtained, washed with water or an appropriate buffer, and the washed cells can be used in the production method of the present invention.

Next, there will be described the plasmid of the present invention and the microorganism of the present invention which has been transformed with the plasmid.

The plasmid of the present invention comprises a DNA fragment containing the gene encoding the enzymes participating in biosynthesis of threonine (threonine operon) which can be expressed in a microorganism requiring biotin in a biotin-requiring microorganism for the growth belonging to coryneform bacteria and a DNA fragment containing a gene encoding autonomous replication in coryneform bacteria cell, as described above.

The DNA fragment containing the gene encoding the enzymes participating in biosynthesis of threonine (threonine operon) which can be expressed in a biotin-requiring microorganism for the growth belonging to coryneform bacteria as mentioned above is contained in, for example, the chromosome of *Escherichia coli* K12 type strain (e.g. ATCC 27325, ATCC 23282, ATCC 23437, etc.).

The DNA fragment containing a gene encoding autonomous replication within coryneform bacteria as mentioned above is contained in, for example, Plasmid pBY502 harboring in *Brevibacterium flavum* MJ-233 (FERM BP-1497) (see Japanese Unexamined Patent Publication No. 36787/1988), Plasmid pBY503 harboring in *Brevibacterium stalionis* IFO 12144 (FERM BP-2525) (see Japanese unexamined Patent Publication No. 95785/1989; this microorganism has been deposited at Fermentation Research Institute, Agency of Industrial Science and Technology, Japan, under the Budapest Treaty).

The plasmid of the present invention can be produced, for example, as follows.

First, the DNA fragment containing the genes encoding the enzymes participating in threonine biosynthesis (threonine operon DNA fragment) is obtained by preparing a chromosomal DNA from *Escherichia coli* K-12 type strain (ATCC 27325, ATCC 23282, ATCC 23437, etc.) excising the threonine operon DNA fragment from the chromosomal DNA with the use of a restriction endonuclease such as BamHI, HindIII, etc., ligating the fragment with BamHI and HindIII sites of the plasmid pBR325 derived from *Escherichia coli*, whereby it is obtained as plasmid pBR325-thr. The DNA fragment containing a gene encoding autonomous replication in coryneform bacteria is obtained from, for example, the plasmid pBY502 as a DNA fragment having a molecular weight of about 4.1 Kb by use of a restriction endonuclease HindIII.

By ligating the DNA fragment of about 4.1 Kb prepared as described above and the DNA fragment of the above plasmid pBR325-thr similarly treated with restriction endonuclease HindIII, the desired plasmid pCRY21thr-1 can be obtained.

By transforming a biotin-requiring microorganism for the growth belonging to coryneform bacteria with the plasmid of the present invention obtained as described above, the microorganism of the present invention can be obtained. As the biotin-requiring microorganism for the growth belonging to coryneform bacteria, *Brevibacterium flavum* MJ-233 (FERM BP 1497) or a strains derived therefrom are preferred as described above.

EXAMPLE

The present invention is described in more detail by referring to the following Examples, by which the scope of the present invention is not limited at all.

In the following Examples, qualitative characteristics of L-threonine were confirmed by Rf value in thin layer chromatogram, mobility in electrophoresis and biological activity value according to microbiological quantitative determination. Quantitation was conducted by using in combination the microbioassay method by use of *Leuconostoc mesenteroides* ATCC8042 and high performance liquid chromatography (Shimadzu LC-5A). In the following Examples, % means % by weight.

EXAMPLE 1

One hundred ml (100 ml) of a medium (urea 0.4%, ammonium sulfate 1.4%, $KH_2PO_4$ 0.05%, $K_2HPO_4$ 0.05%, $MgSO_4.7H_2O$ 0.05%, $CaCl_2.2H_2O$ 2 ppm, $FeSO_4.7H_2O$ 2 ppm, $MnSO_4.4-6H_2O$ 2 ppm, $ZnSO_4.7H_2O$ 2 ppm, NaCl 2 ppm, biotin 200 µg/liter, thiamine hydrochloride 100 µg/liter, casamino acid 0.1%, yeast extract 0.1%) was apportioned into an Erlenmyer's flask of 500 ml volume, and after sterilization (pH 7.0 after sterilization), *Brevibacterium flavum* MJ-233 (FERM BP-1497) was inoculated and 2 ml of ethanol was aseptically added, followed by shaking culture at 30° C. for 2 days.

Next, 1000 ml of the main culture medium (ammonium sulfate 2.3%, $KH_2PO_4$ 0.05%, $K_2HPO_4$ 0.05%, $MgSO_4.7H_2O$ 0.05%, $FeSO_4.7H_2O$ 20 ppm, $MnSO_4.n-H_2O$ 20 ppm, biotin 200 µg/liter, thiamine hydrochloride 100 µg/liter, casamino acid 0.3%, yeast extract 0.3%) was charged into a 2-liter volume aerating stirring tank, and after sterilization (120° C., 20 minutes), 20 ml of ethanol and 20 ml of the above pre-cultured product were added, and cultivation was conducted at 1000 rpm, under aeration of 1 vvm, a temperature of 33° C. and pH 7.6 for 48 hours.

Ethanol was added intermittently every 1 to 2 hours so that the ethanol concentration in the medium did not exceed 2 vol. % during cultivation.

After completion of cultivation, cells were collected by centrifugation from 300 ml of the cultured product, and the cells washed twice with distilled water were suspended in 1000 ml of a reaction mixture [DL-aspartic acid 2 mg, pyridoxalphosphoric acid 5 µg, phosphate buffer 100 µmoles, ethanol 10 mg, pH 7.6, contained in 1 ml of reaction mixture], and then said suspension was charged into a 2-liter volume aerating stirring tank. Then, 20 ml of ethanol was added and the reaction was carried out at 300 rpm, an aeration of 0.1 vvm, a temperature of 33° C. and pH 7.6 for 10 hours.

After completion of the reaction, L-threonine in the supernatant free of microorganisms by centrifugation (4000 rpm, 15 minutes, 4° C.) was quantitated. Also, 500 ml of the reaction mixture after completion of the reaction was passed through a column of a strongly, acidic cation exchange resin ($H^+$ form) to have L-threonine adsorbed thereon, washed with water and then eluted with 0.5N ammonia water. Then, L-threonine fractions were concentrated and crystals of L-threonine were precipitated with cold ethanol. The results are shown in Table 1 shown below.

TABLE 1

| Amount of L-threonine formed (mg/l) | Amount of L-threonine purified (mg) |
|---|---|
| 220 | 71 |

EXAMPLE 2

*Brevibacterium flavum* MJ-233-AB-41 (FERM BP-1498) was cultured under the same conditions as in Example 1, and after the reaction was carried out under the same conditions as in Example 1, L-threonine in the supernatant was quantitated. Further crystals of L-threonine were precipitated in the same operation as in Example 1. The results are shown in Table 2.

TABLE 2

| Amount of L-threonine formed (mg/l) | Amount of L-threonine purified (mg) |
|---|---|
| 240 | 75 |

EXAMPLE 3

*Brevibacterium flavum* MJ-233-ABT-11 (FERM BP-1500) was cultured under the same conditions as in Example 1, and after the reaction was carried out under the same conditions as in Example 1, L-threonine in the supernatant was quantitated. Further crystals of L-threonine were precipitated in the same operation as in Example 1. The results are shown in Table 3.

TABLE 3

| Amount of L-threonine formed (mg/l) | Amount of L-threonine purified (mg) |
|---|---|
| 235 | 74 |

EXAMPLE 4

*Brevibacterium flavum* MJ-233-ABD-21 (FERM BP-1499) was cultured under the same conditions as in Example 1, and after the reaction was carried out under the same conditions as in Example 1, L-threonine in the supernatant was quantitated. Further crystals of L- threonine were precipitated in the same operation as in Example 1. The results are shown in Table 4.

TABLE 4

| Amount of L-threonine formed (mg/l) | Amount of L-threonine purified (mg) |
|---|---|
| 226 | 72 |

EXAMPLE 5

The same operation as in Example 1 was practiced except for replacing ethanol added during the reaction with glucose. The glucose concentration was made 2%. The amount of L-threonine formed in the supernatant after completion of the reaction and the amount purified are shown in Table 5.

TABLE 5

| Amount of L-threonine formed (mg/l) | Amount of L-threonine purified (mg) |
|---|---|
| 230 | 73 |

EXAMPLE 6

The same operation as in Example 1 was practiced except for replacing the reaction mixture used during the reaction in Example 1 with $(NH_4)_2SO_4$ 2 g/l; $KH_2PO_4$ 0.5 g/l; $K_2HPO_4$ 0.5 g/l; $MgSO_4.7H_2O$ 0.5 g/l; $FeSO_4.7H_2O$ 20 ppm, $MnSO_4.4-6H_2O$ 20 ppm; thiamine hydrochloride 100 µg/l; DL-aspartic acid 2 g/l (pH 7.6).

The amount of L-threonine formed in the supernatant after completion of the reaction and the amount purified are shown in Table 6.

TABLE 6

| Amount of L-threonine formed (mg/l) | Amount of L-threonine purified (mg) |
|---|---|
| 250 | 81 |

EXAMPLE 7

Construction of Plasmid pCRY21thr-1

(A) Preparation of Plasmid pBY502

Plasmid pBY 502 is a plasmid having a molecular weight of about 30 megadaltons separated from *Brevibacterium flavum* MJ-233 (FERM BP-1497), which is a plasmid disclosed in Japanese Unexamined Patent Publication No. 36787/1988. Plasmid pBY 502 was prepared as described below.

In the one liter of a semi-synthetic medium A (urea 2 g, $(NH_4)_2SO_4$ 7 g, $K_2HPO_4$ 0.5 g, $KH_2PO_4$ 0.5 g, $MgSO_4$ 0.5 g, $FeSO_4.7H_2O$ 6 mg, $MnSO_4$ 4-6 mg, $H_2O$ 6 mg, yeast extract 2.5 g, casamino acid 5 g, biotin 200 µg, thiamine hydrochloride 200 µg, glucose 20 g, pure water one liter) was cultured *Brevibacterium flavum* MJ-233 (FERM BP-1497) to the later stage of the logarithmic growth phase, and the cells were collected. The cells obtained were suspended in 20 ml of a buffer [25 mM Tris(hydroxymethyl)aminomethane, 10 mM EDTA, 50 mM glucose] containing lysozyme (a final concentration of 10 mg/ml), and the reaction was carried out at 37° C. for one hour. To the reaction mixture was added 40 ml of an alkali-SDS solution [0.2N NaOH, 1% (w/v) SDS), followed by gentle mixing, and the mixture was left to stand at room temperature for 15 minutes.

Next, to the reaction mixture was added 30 ml of a potassium acetate solution [mixed solution of 5M potassium acetate solution 60 ml, acetic acid 11.5 ml, pure water 28.5 ml] and after thorough mixing, the mixture was left to stand in ice-water for 15 minutes. The total amount of the lyzed product was transferred to a centrifuge tube, and subjected to centrifugation of 15,000×g at 4° C. for 10 minutes to give a supernatant.

To the supernatant was added equal amount of a phenol.chloroform mixture (phenol chloroform 1:1 mixture) to give a suspension, which was then transferred into a centrifuge tube and subjected to centrifugation of 15,000×g at room temperature for 5 minutes, followed by recovery of the aqueous layer. To the aqueous layer was added two-fold amount of ethanol, and after left to stand at −20° C. for one hour, the mixture was subjected to centrifugation of 15,000×g at 4° C. for 10 minutes, and the precipitates were recovered.

The precipitates were dried under reduced pressure and then dissolved in 2 ml of a TE buffer [Tris 10 mM, EDTA 1 mM, adjusted to pH 8.0 with HCl]. To the solution were added 15 ml of a cesium chloride solution [a solution containing 170 g of cesium chloride in 100 ml of a TE buffer of 5-fold concentration] and 1 ml of a 10 mg/ml ethidium bromide solution to adjust the density to 1.392 g/ml. The solution was subjected to centrifugation of 116,000×g at 12° C. for 42 hours.

Plasmid pBY502 is found as the lower band in the centrifuge tube by UV-ray long wave irradiation. By withdrawing the band with a synringe from the side of the centrifuge tube, a fraction containing plasmid pBY502 was obtained. Subsequently, the fraction was treated with equal amount of isoamyl alcohol for 4 times to remove ethidium bromide by extraction, and then dialyzed against TE buffer. To the dialysate containing plasmid pBY502 thus obtained was added 3M sodium acetate solution so as to give the final concentration of 30 mM, then added with 2-fold amount of ethanol and left to stand at −20° C. for one hour. The solution was subjected to centrifugation of 15,000×g to precipitate DNA, and about 20 µg of plasmid pBY502 was obtained.

(B) Preparation of Chromosomal DNA of *Escherichia coli* ATCC 27325

One hundred (100) ml of L-medium (trypton 10 g, yeast extract 5 g, glucose 1 g, NaCl 5 g, distilled water 1 liter, pH 7.2) was apportioned into an Erlenmeyer's flask of 500 ml volume, and sterilized at 120° C. for 15 minutes. Into the medium was inoculated *Escherichia coli* ATCC 27325, and after cultivation was carried out at 37° C. for 15 hours, 2 ml of the culture broth was collected and inoculated newly into 100 ml of the above culture medium, followed again by culturing at 37° C. for 4 hours.

After completion of cultivation, the total amount of the culture broth was subjected to centrifugation (8000×g, 15 minutes, 4° C.) to collect the cells, which were suspended in 50 ml of 50 mM Tris buffer (pH 8.0) - 10 mM EDTA 2Na solution. Next, lysozyme was added so as to give the final concentration of 2 mg/ml and, after left to stand for 5 minutes, 6 ml of 10% sodium dodecylsulfate was added, followed by incubation at 65° C. for 30 minutes. To the lyzed solution, 15 ml of 5M NaCl solution was added, cooled at 0° C. for 1 hour, and the total amount of the mixture was subjected to centrifugation (12,000×g, 60 minutes, 4° C.) The supernatant fraction was collected, diluted with 2-fold amount of ethanol and after mixing subjected to centrifugation (5,000×g, 10 minutes, 4° C.). The precipitates obtained were dissolved in 10 mM Tris buffer (pH 7.5) - 1 mM EDTA 2Na solution, and subjected to the phenol treatment (protein removal treatment) and the treatment with ribonuclease, to give finally 1.5 mg of DNA.

(C) Preparation of the threonine operon DNA fragment

Plasmid pBR325 is a plasmid having a molecular weight of 3.4 megadaltons which is replicated within *Escherichia coli* and exhibits chloramphenicol, tetracycline, ampicillin resistance, and commercially available from SIGMA CHEMICAL COMPANY.

An amount of 25 μg of the chromosomal DNA prepared in the above (A) was cleaved by digestion with restriction endonuclease HindIII and BamHI (50 units of each) at 30° C. for one hour to prepare a solution of HindIII and BamHI digested products of the chromosomal DNA. The digested product solution was mixed with a digested product solution obtained by cleaving 1 μg of plasmid pBR325 by digestion with restriction endonuclease HindIII and BamHI (one unit of each) at 30° C. for one hour, and one unit of the respective components of 50 mM Tris buffer (pH 7.6), 10 mM dithiothreitol, 1 mM ATP, 10 mM $MgCl_2$ and $T_4$ DNA ligase were added (the concentrations of the respective components are final ones) to carry out the reaction at 16° C. for 15 hours to effect ligation.

By use of this solution, according to the conventional method [see M. Mandel, A. Higa: J. Mol. Biol., 53, 159 (1970)], *Escherichia coli* K12 strain (ATCC 23728 L-threonine requirement, L-leucine requirement, thiamine requirement), was transformed and spread onto a selective medium ($K_2HPO_4$ 7 g, $KH_2PO_4$ 2 g, $(NH_4)_2SO_4$ 1 g, $MgSO_4$ $7H_2O$ 0.1 g, L-leucine 50 mg, thiamine hydrochloride 50 mg, glucose 2 g, chloramphenicol 10 mg, agar 20 g, distilled water one liter). The strain grown on the culture medium was inoculated into a medium containing 30 μg/ml as the final concentration of chloramphenicol in L-medium, and the plasmid was extracted from the grown strains according to the alkali-SDS method [see T. Maniatis, E. F. Fritsch, J. Sambrook: "Molecular cloning" (1982) p. 90–91]. When the plasmid was cleaved with restriction endonuclease BamHI and HindIII and its molecular weight was examined with the use of Agarose gel, DNA of about 6.0 Kb was found to be inserted at HindIII and BamHI sites of plasmid pBR325.

Further, when the above host was retransformed with the plasmid solution, strains growing in the selective medium at a frequency of about $10^5$ cells/μg DNA appeared.

(D) Construction of plasmid pCRY21thr-1

Plasmid pBY502 (10 μg) obtained in (A) was digested by the reaction at 37° C. for 2 hours with the use of a restriction endonuclease HindIII (50 units).

Also, 0.5 μg of the plasmid pBR325thr obtained in (C) was digested by the reaction at 37° C. for one hour with a restriction endonuclease HindIII (5 units).

Subsequently, the both digested products were mixed, and the restriction endonuclease was inactivated by heating at 65° C. for 10 minutes, and the respective components in said inactivated solution were fortified so as to give the final concentrations of 50 mM Tris buffer pH 7.6, 10 mM $MgCl_2$, 10 mM dithiothreitol, 1 mM ATP and $T_4$ ligase 1 unit, respectively, followed by incubation at 16° C. for 15 hours, to effect ligation of DNA.

(E) Preparation of protoplast

A plasmid BY502 cured strain of *Brevibacterium flavum* MJ-233 plasmid was cultured in 100 ml of the above A medium to the initial stage of logarithmic growth phase, penicillin G was added so as to give a final concentration of 0.2 unit/ml, and further shaking culture was conducted for 2 hours. The microorganism cells were collected by centrifugation, the cells were washed with 50 ml of a TSMC buffer comprising 0.5M sodium succinate, 20 mM Tris(hydroxymethylaminomethane), 20 mM calcium chloride, 20 mM magnesium chloride (pH 7.5), then suspended in 10 ml of a TSMC buffer containing 4 mg/ml lysozyme, 1000 unit/ml achromopeptidase to effect protoplast formation by the reaction at 30° C. for 16 hours. After completion of the reaction, the product was centrifuged at 3000 rpm for 10 minutes and then the protoplast was washed with 20 ml of TSMC buffer, and again suspended in 3 ml of TSMC buffer.

(F) Transformation

The protoplast obtained in (E) (200 μl) and the DNA ligation mixture obtained in (D) were mixed together and, after ice-cooling, polyethylene glycol 6000 was added so as to give a final concentration of 20%. Then, the mixture was ice-cooled for about 3 minutes, added with 5 ml of a TSMC buffer, subjected to centrifugation (3000 r.p.m., 10 minutes) and then resuspended in 3 ml of A medium containing 0.5M sucrose, followed by incubating at 30° C. for 2 hours.

The culture broth was spread onto a regeneration medium containing 7 μg/ml (final concentration) of chloramphenicol (urea 2 g, $(NH_4)_2SO_4$ 7 g, $KH_2PO_4$ 0.5 g, $K_2HPO_4$ 0.5 g, $MgSO_4.7H_2O$ 0.5 g, $FeSO_4.7H_2O$ 6 mg, $MnSO_4.4$–$6H_2O$ 6 mg, yeast extract 2.5 g, casamino acid 7.5 g, biotin 200 μg, thiamine hydrochloride 200 μg, sucrose 171 g, glucose 5 g, gelatin 15 g, agar (DIFCO) 8 g, the total amount fill up to one liter with distilled water). After incubation at 30° C. for 3–15 days, the colony appeared was transferred into A medium containing 7 μg/ml of chloramphenicol, and the phenotype of chloramphenicol resistance was confirmed.

(G); From the chloramphenicol resistance strain obtained in (F), a plasmid was prepared according to the method of (A). The plasmid was subjected to measurements of molecular weight with various restriction endonucleases (Table 7).

TABLE 7

| Restriction endonucleases | Number of recognition sites | Molecular weight megadalton |
|---|---|---|
| Hind III | 2 | 2.7 (4.1), 7.2 (11.1) |
| BamH I | 2 | 3.8 (5.8), 6.1 (9.4) |
| Sma I | 1 | 9.9 (15.2) |
| Sal I | 4 | 0.85 (1/3), 0.95 (1.4), 3.9 (6.0), 4.2 (6.5) |
| Pst I | 1 | 9.9 (15.2) |
| EcoR I | 2 | 3.9 (6.0), 6.0 (9.2) | value in parentheses shows Kb.

The plasmid characterized by the above restriction endonucleases was designated as pCRY21thr-1.

(H) Introduction of plasmid pCRY21thr-1 into *E. coli*

Competent cells of *Escherichia coli* $K_{12}$ type strain (ATCC 23738) prepared according to conventional method (M. Mandel, A. Higa: J. Mol. Biol. 53, 159 (1970)) were transformed with the plasmid pCRY2thr-1 and spread onto the selective medium as described in (C), whereby transformed cells were obtained at a frequency of $10^5$ cells/1 μg of pCRY2thr-1. Further, 10 strains of the transformed cells were transferred into L-medium containing 30 μg/ml as the final concentration of chloramphenicol, and the plasmid was extracted by the alkali-SDS method, cleaved with various restriction endonucleases and its molecular weight was measured according to Agarose gel electrophoresis to be equal to that of the plasmid pCRY2thr-1 (Table 7) obtained from the transformed cell of *Brevibacterium flavum*. This indicates that pCRY2thr-1 is the plasmid which can replicate within *Brevibacterium flavum* MJ-233 which is a kind of coryneform bacteria and *Escherichia coli*, and further that the plasmid pCRY21thr-1 obtained from the transformed *Brevibacterium flavum* MJ-233 contains threonine operon derived from *E. coli*.

The *Brevibacterium flavum* MJ-233GE1002 transformed with the plasmid pCRY21thr-1 was deposited at Institute of Fermentation Research, Agency of Industrial Science and Technology, 1-3, Higashi 1-chome, Tsukuba-shi, Ibaraki prefecture, Japan, on Sep. 13, 1988, under the Budapest Treaty the deposition No. FERM BP-2050 domestic deposition No. FERM P-9803).

EXAMPLE 8

The same procedure was carried out as in Example 1 except that *Brevibarium flavum* MJ-233 GE1002 (FERM BP-2050) was used in place of *Brevibarium flavum* MJ-233 (FERM BP-1497) in Example 1. Results are shown in Table 8.

TABLE 8

| Amount of L-threonine formed (mg/l) | Amount of L-threonine purified (mg) |
|---|---|
| 310 | 99 |

EXAMPLE 9

The same operation as in Example 8 was practiced except for replacing ethanol added during the reaction with glucose. The glucose concentration was made 2%. The amount of L-threonine formed in the supernatant after completion of the reaction and the amount purified are shown in Table 9.

TABLE 9

| Amount of L-threonine formed (mg/l) | Amount of L-threonine purified (mg) |
|---|---|
| 300 | 95 |

EXAMPLE 10

The same operation as in Example 8 was practiced except for replacing the reaction mixture used during the reaction in Example 8 with $(NH_4)_2SO_4$ 2 g/l; $KH_2PO_4$ 0.5 g/l; $K_2HPO_4$ 0.5 g/l; $MgSO_4.7H_2O$ 0.5 g/l; $FeSO_4.7H_2O$ 20 ppm, $MnSO_4.4-6H_2O$ 20 ppm; thiamine hydrochloride 100 μg/l; DL-aspartic acid 2 g/l (pH 7.6).

The amount of L-threonine formed in the supernatant after completion of the reaction and the amount purified are shown in Table 10.

TABLE 10

| Amount of L-threonine formed (mg/l) | Amount of L-threonine purified (mg) |
|---|---|
| 340 | 109 |

We claim:

1. A process for producing L-threonine, comprising:
   (i) subjecting L- or DL-aspartic acid or a salt thereof to enzymatic reaction with ethanol or glucose, in a biotin-free aqueous solution in the presence of cells of biotin-requiring microorganism *Brevibacterium flavum* MJ-233, FERM BP-1497 or a mutant strain derived therefrom capable of producing L-threonine under these conditions, and
   (ii) recovering L-threonine from the reaction mixture.

2. The process as claimed in claim 1, wherein said biotin-requiring microorganism is one member selected from the group consisting of:
   *Brevibacterium flavum* MJ-233 (FERM BP-1497),
   *Brevibacterium flavum* MJ-233-AB-41 (FERM BP-1498),
   *Brevibacterium flavum* MJ-233-ABT-11 (FERM BP-1500),
   *Brevibacterium flavum* MJ-233-ABD-21 (FERM BP-1499), and
   *Brevibacterium flavum* MJ-233-GE1002 (FERM BP-2050).

* * * * *